United States Patent
McGushion

(10) Patent No.: US 9,066,778 B2
(45) Date of Patent: Jun. 30, 2015

(54) MASSAGE DEVICE HAVING A HEAT RESERVOIR

(71) Applicant: Aaron Paul McGushion, Seal Beach, CA (US)

(72) Inventor: Aaron Paul McGushion, Seal Beach, CA (US)

( * ) Notice: Subject to any disclaimer, the term of this patent is extended or adjusted under 35 U.S.C. 154(b) by 0 days.

(21) Appl. No.: 14/217,443

(22) Filed: Mar. 17, 2014

(65) Prior Publication Data

US 2014/0276255 A1 Sep. 18, 2014

Related U.S. Application Data

(60) Provisional application No. 61/791,104, filed on Mar. 15, 2013.

(51) Int. Cl.
| | |
|---|---|
| A61H 1/00 | (2006.01) |
| A61H 1/02 | (2006.01) |
| A61H 5/00 | (2006.01) |
| A61F 7/00 | (2006.01) |
| A61F 7/02 | (2006.01) |
| A61F 7/08 | (2006.01) |
| A61F 7/10 | (2006.01) |

(52) U.S. Cl.
CPC .. *A61F 7/00* (2013.01); *A61H 1/00* (2013.01); *A61F 7/02* (2013.01); *A61F 7/08* (2013.01); *A61F 2007/0087* (2013.01); *A61F 2007/0095* (2013.01); *A61F 2007/0242* (2013.01); *A61F 2007/108* (2013.01)

(58) Field of Classification Search
CPC .............. A61H 2201/02; A61H 2201/0207; A61H 2201/0214; A61H 23/00; A61H 2023/002; A61H 23/004; A61H 23/006
USPC ............ 601/15, 17, 134, 135, 138, 148, 154, 601/159
See application file for complete search history.

(56) References Cited

U.S. PATENT DOCUMENTS

| | | | | |
|---|---|---|---|---|
| 2,709,432 | A * | 5/1955 | Ackerman | 401/217 |
| 5,727,556 | A * | 3/1998 | Weth et al. | 600/439 |
| 5,997,380 | A * | 12/1999 | Yang | 450/57 |
| 6,499,485 | B1 * | 12/2002 | Pepera | 128/845 |
| 6,679,857 | B1 | 1/2004 | Bastia et al. | |
| 6,758,826 | B2 | 7/2004 | Luettgen et al. | |
| 7,211,057 | B2 | 5/2007 | Gleason et | |
| 7,244,237 | B2 * | 7/2007 | Smith | 601/15 |
| 2004/0210175 | A1 * | 10/2004 | Robbins et al. | 601/134 |
| 2006/0224091 | A1 * | 10/2006 | Boys | 601/78 |
| 2010/0274162 | A1 * | 10/2010 | Evans | 601/15 |
| 2012/0022374 | A1 * | 1/2012 | Weth | 600/439 |

\* cited by examiner

*Primary Examiner* — Kristen Matter

(57) ABSTRACT

A massage device is provided with a pouch containing a liquid medium and a massage prong for imparting massage pressure on the person's body during a massage. The pouch is configured for application to the body such that it covers an area on the body substantially larger than the massage prong. The massage prong operates and applies a force to the body through the wall of the pouch. The massage prong is permitted to move within at least a portion of the area without substantial movement of the pouch relative to the body. A lubricating layer sealed present massager can provide a relaxing and therapeutic heated or cooled massage over a large area of the body while reducing pinching and friction between the skin and the massage prong.

13 Claims, 4 Drawing Sheets

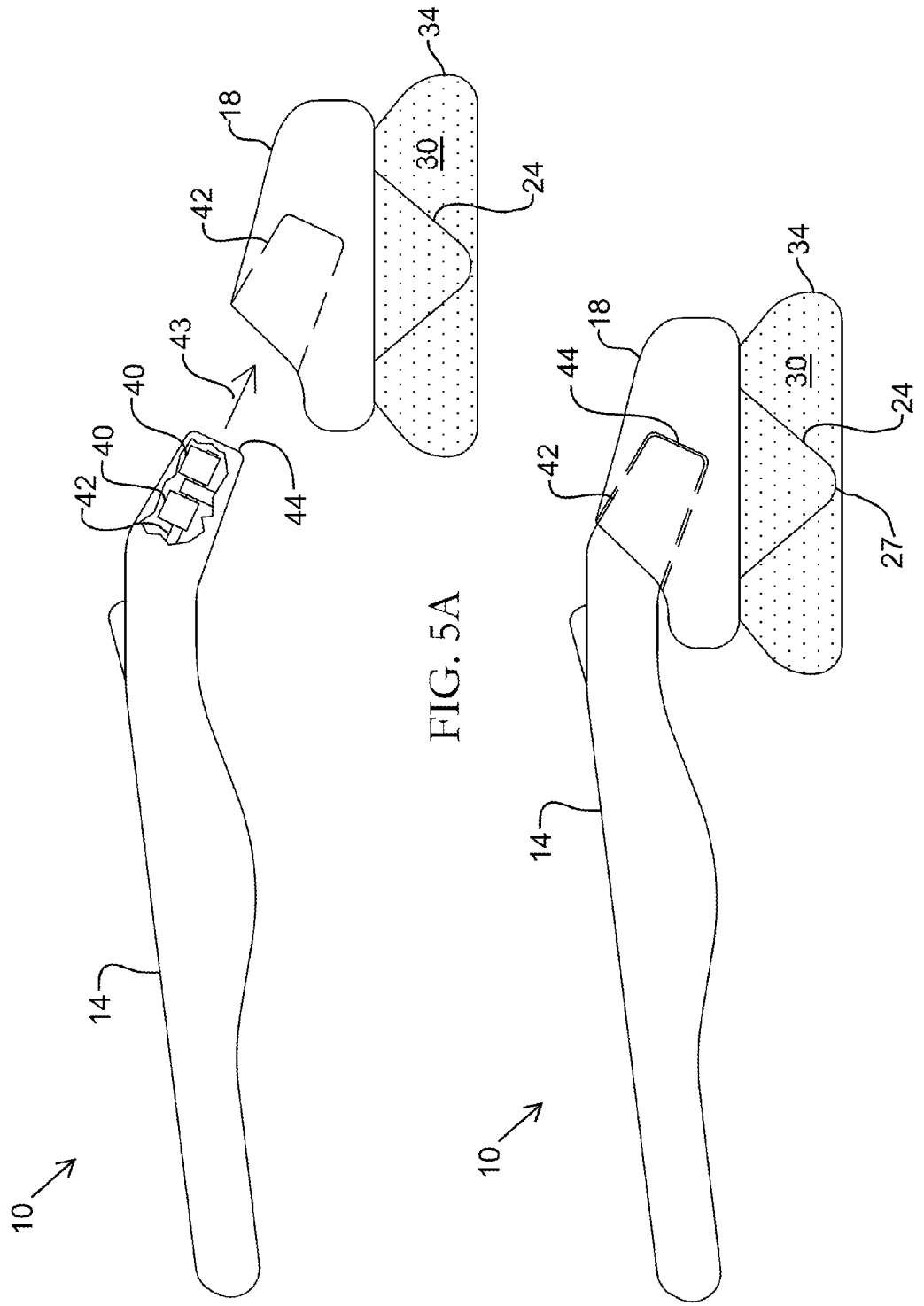

MASSAGE DEVICE HAVING A HEAT RESERVOIR

RELATED APPLICATION DATA

This application claims the priority date of provisional application no. 61/791,104 filed on Mar. 15, 2013.

BACKGROUND

This invention relates to a massage device, more particularly to a device and method for providing a temperature controlled massage over an area of the skin.

It is a desire when designing a massage device to provide a massage tip, prong, or head that maximizes massage comfort, therapeutic value, and temperature control. Current massage devices utilize various means to achieve these goals.

For example, U.S. Pat. No. 6,679,857 to Bastia et al. shows a massager with a resilient gel pad covering the permanently attached head of the massager. The pad is designed to provide a soft, distributed massage, where the gel pad is resilient (i.e., elastic, such that it springs back to its original shape). The silicon-based pad is preferably solid in nature, so that the vibration provided by the driver is transmitted through the pad and to the user's skin. A hard rubber node may be separately integrated to the head so that the user can rotate the head to alternate between using the gel pad and hard node.

Looking now at U.S. Pat. No. 7,211,057 to Gleason et al., a massager is shown that has two hard, plastic massage heads, one integrated with the handle and another head that selectively attaches over the first head. The two heads can be either heated or cooled (one usually opposite the other), where a heated massage can be first provided by the first head and a cooled massage provided by attaching the second head thereafter. Within the second detachable head a pocket can be created in which a hot or cold gel insert can be placed. The gel insert heats or cools the body of the second head to provide a hot or cold massage. The second head is attached to the first head by holding it to the first head and threading a thumb-screw.

Yet another means to increase user comfort is seen in U.S. Pat. No. 6,758,826 to Luettgen et al., where a J-shaped massager is shown that supports several massage tips to permit the user to massage multiple parts of his or her own body. These tips are removable and a variety of tips are shown. One tip has a gel layer or thin cover that is placed overtop the hard tip. This tip or just the cover itself can be heated or cooled. However, a thin layer provides heat for just a short period and provides heat to a small area of skin just beneath the tip itself. Further, to massage a larger area, the tip must be moved relative to the skin, increasing pinching and friction, overall adding to discomfort.

SUMMARY

A massage device for massaging a surface area of a body is provided. The massage device is primarily comprised of a massage prong and a pouch containing a liquid medium within a reservoir. The tip of the massage prong imparts a massage pressure on the surface area. The pouch has a bottom surface and a flexible sidewall connected to a frame. The massage prong is situated above the bottom surface with the bottom surface positioned between the tip of the massage prong and the surface area of the body when in use, so that the massage pressure is imparted through the bottom surface.

When in use, the pouch is positioned upon the surface area of the body with the bottom surface contacting the surface area, either directly contacting the skin, hair, etc. or contacting the surface area through clothing, towel, etc. The bottom surface has an area substantially larger than the tip of the massage prong such that the tip can be moved laterally on the bottom surface with the side wall deforming with the movement of the tip, so that the bottom surface remains substantially stationary relative to the surface area of the body. In this way, a large portion of the body can be massaged by moving the handle and massage prong, but without substantially moving the pouch relative to the body.

Optionally, the massage prong can be immersed within the liquid medium and permitted to move within the liquid medium. A second reservoir may be optionally formed between the reservoir and the bottom surface, the second reservoir containing a lubricant. Optionally, the frame supports the pouch and massage prong, where the frame is detachable from a handle and the handle has a massage driver. When the frame is detached from the handle, the pouch may be brought in thermal contact with one of a heat source and a cold source.

The massage driver may be optionally located within the handle at a terminus, where the frame is configured to receive the terminus, such that the massage driver is proximally located to the frame. As an option, thermochromatic ink can be distributed within the liquid medium, such that the color of the liquid medium changes in response to temperature. The liquid medium of the pouch can be brought to a temperature different than the body temperature, where the application of the pouch to the body affects the body temperature, by warming or cooling the body temperature at the massage area.

Optionally, the frame has an prong opening for receiving the prong, with the prong being attachable to the handle and being detachable from the frame. The prong may be temporarily or permanently attached to the handle. A top surface extends across the prong opening to form a prong cavity. When the frame is attached to the handle the prong extends though the prong opening and into the prong cavity, with the tip of the prong acting through the top surface so that the massage pressure is imparted through the top surface and the bottom surface. The massage driver is optionally one of a percussive driver and an offset weight driver.

A method for using a massage device is additionally provided, by first providing a massage device with a pouch and a liquid medium sealed within the pouch, with a massage prong immersed within the pouch and capable of moving through the liquid medium relative to a wall of the pouch. Next, changing the temperature of the liquid medium by bringing the pouch in thermal contact with a thermal source, such as a microwave, refrigerator, or thermal plate. Then, applying the pouch to a surface area of a body. And, imparting a massage force on the body by the massage prong operating though the wall and laterally moving relative to the wall. Optionally, the frame can be detached from the handle before bringing the pouch in thermal contact with a thermal source. The frame is reattached to the handle before applying the pouch to the surface area of the body.

BRIEF DESCRIPTION OF THE SEVERAL VIEWS OF THE DRAWINGS

FIG. 5A-B is a side plan views of yet another embodiment of the massager, showing the handle with offset driver being inserted into a pocket formed in the massage head.

DETAILED DESCRIPTION

Figure 1A:
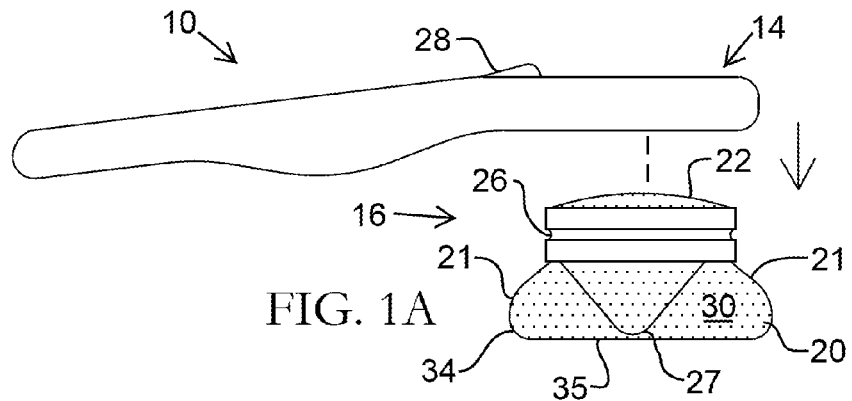
FIGS. 1A-B are top and side plan views of an embodiment of the massager, showing the detachable massage head.
Figure 1B:
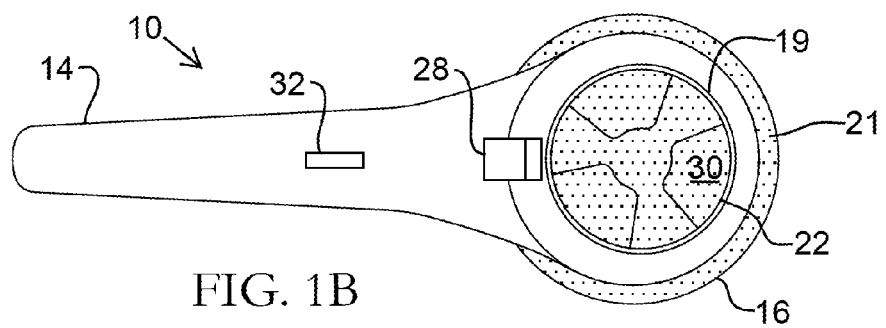
Figure 1C:
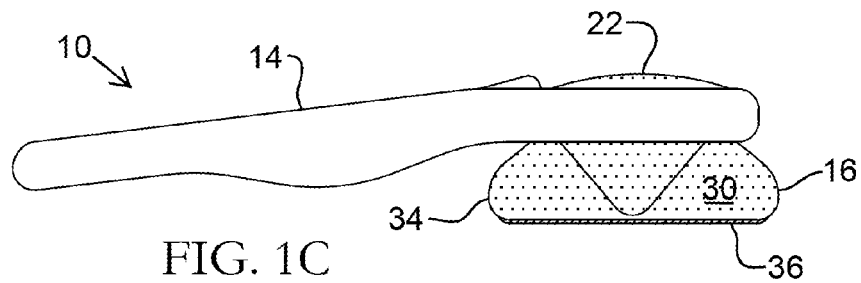
FIG. 1C is a side plan views of an embodiment of the massager, showing the massage head with a second lubricant reservoir.
Figure 2:
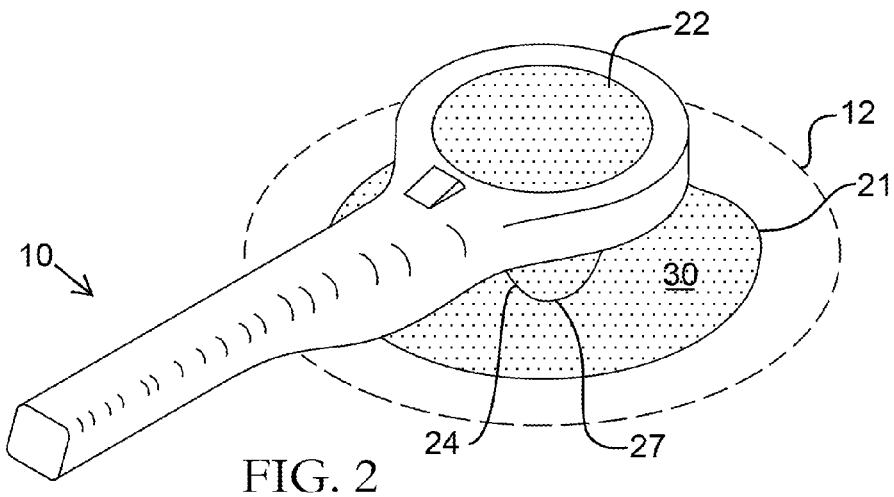
FIG. 2 is a perspective view from above of an embodiment of the massager, showing its application to a user's skin.

Looking at FIGS. 1A-C, the massager (10) is comprised of a handle (14) that is detachable from the massage head (16). The handle (14) interior (as seen generally in FIG. 6) is sufficiently sized to contain the electronic portions of the device, such as the driver motor or other massage impact, percussion, or vibration means, the battery (if battery operated), the circuit board, switch, and other miscellaneous wiring and circuitry. The massage head (16) preferably is comprised of a frame (18) that can provide a rigid and secure connection to the handle (14), at least one massage prong (24) and a heat reservoir (20) filled with a medium (30) that permits movement of the massage prong (24) through the medium and has the ability to store heat.

Preferably, the medium (30) is a water/glycerine-based fluid (e.g., water, glycerine, methyl paraben and neutralized carbopol resin), a saline or brine solution, other similar medium, or a particulate medium such as beads and the like. The essential feature of the medium (30) is the ability to store heat or have heat removed therefrom. Thus, there are numerous materials that may suitably perform as a heat medium. Heat may be added to the medium (30) through use of a microwave, heat element, heat plate, boiling water, hot temperature reservoir, or any other means known in the art. Heat may be removed from the medium (30) through use of a refrigeration means, or through any other thermal contact with a cold temperature reservoir. Thermochromatic ink may be added to the medium (30), such that if the medium is too hot (scalding) a color change can indicate this to the user. For example, the medium (30) may be colored blue when cool and may turn red when heated above a certain temperature.

The medium (30) is contained within a flexible, plastic pouch (34) that permits the conforming of the pouch (34) to the surface of the skin (12), permits containment of the medium (30), and permits the transfer of massage pressure and activity from the massage prong (24) to the skin (12). The pouch (34) may additionally be made of any appropriate material, whether translucent, transparent, or opaque (such as plastic-lined cloth, nylon, or the like). The side wall (21) of the pouch (34) is generally flexible to permit the frame (18) with the massage prong (24) to move laterally relative to the bottom surface (35), where the bottom surface (35) remains stationary on the surface of the skin (12). For example, the bottom surface (35) can have a diameter from about 1 inch to about 8 inches and the tip (27) of the massage prong (24) can have a diameter from about 0.5 inches to about 1.5 inches. Thus, the diameter of the bottom surface is preferably at least double the diameter of the tip (27) to permit the massage prong (24) to freely travel over a large area, while the bottom surface remains in stationary contact with the surface of the skin (12). If the tip (27) or bottom surface (35) are not circular, then a width measurement and ratio can be used in place of the diameter measurement and ratio.

In one example, the diameter of the tip (27) is approximately 0.5 inches and the diameter of the bottom surface (35) is approximately 3 inches. In this example, the area of the bottom surface is approximately 28 inches squared, compared to the area of the tip (27), which is approximately 0.8 inches squared. Because the side wall (21) is flexible, the tip (27) can laterally travel over the large area of the bottom surface (35) while the bottom surface is stationary on the skin (12). The bottom surface (35) is generally flexible too, so that when the tip (27) is moved, for example, to the far right, a portion of the bottom surface (35) on the left side will lift from the skin (12) slightly to permit the tip (27) to move to the right yet further. When the user desires, the pouch (34) can be lift or slid to a new location on the skin surface (12).

FIG. 1C shows an alternate embodiment, where a second reservoir (36) is provided by sealing a second ply of plastic to the bottom surface (35) of pouch (34) to provide a interstice between the bottom of the pouch (34) and the second ply that is filled with a lubricating fluid, such as mineral oil to reduce massage friction. The ply associated with the pouch (34) may thereby move somewhat independently of the ply of the second reservoir (36), as the two surfaces would be permitted to slide relative to one another within the bounds of the physical constraints of their seal. Further, the lubricating fluid is heated or cooled along with the medium (30), and heat may transfer between the medium (30) and the lubricating fluid.

In this embodiment, the massage head (16) has an annular frame (18) with a clear window (22) above the prong (24), which may optionally be made of a flexible or rigid plastic. The clear window (22) is to provide the user visual access to the massage prong (24) and the portion of skin (12) being massaged. The prong (24) is additionally provided with three visual ports or cutouts to facilitate viewing of the skin from above, if desired. The frame (18) may connect to the handle in numerous ways well known in industry. In the illustrated example, the frame (18) is provided with an annular groove (26) that connects with a retractable detent ball (not visible) that is controlled by the release button (28). The annular frame (18) fits within an opening (19) formed in the handle (14). The detent ball is located within the opening (19) and is normally spring loaded to extend into the opening. When the release button (28) is drawn back, the detent ball retracts to provide clearance so that the annular frame (18) can be inserted within the opening (19). When the release button (28) is released, the detent ball extends into the opening (19) and engages the annular groove (26) of the annular frame (18). A power switch (32) or wheel (such as a potentiometer) may be used to control the power and intensity of the massage provided.

Figure 3A:
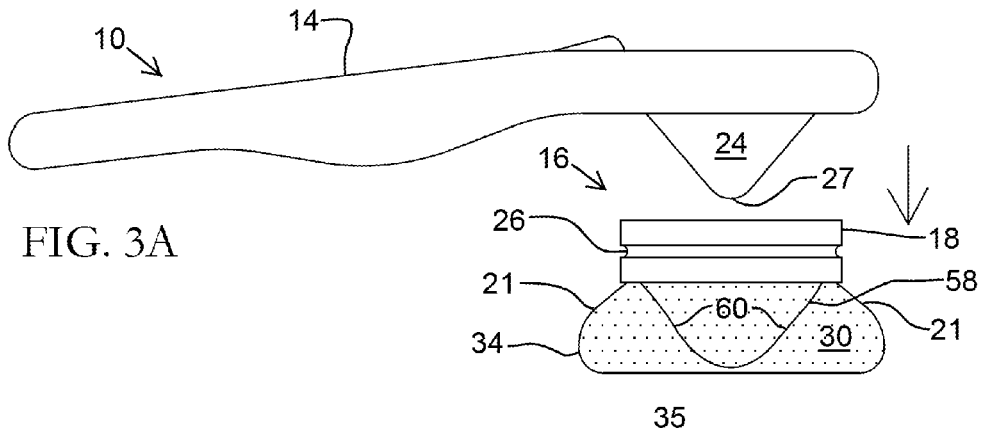
FIGS. 3A-B is a side plan view of another embodiment of the massager, showing the massage head with the pouch in cross-section.
Figure 3B:
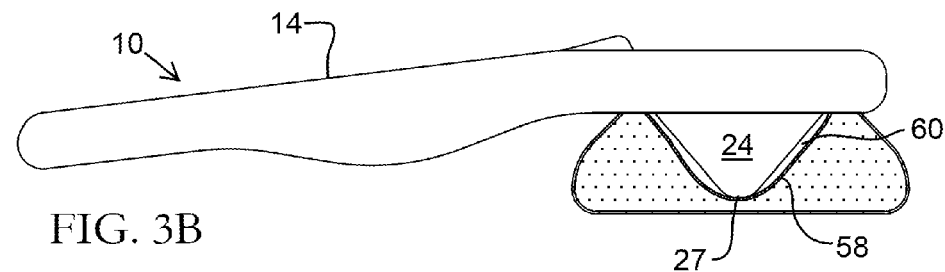

FIG. 3, shows yet another alternate embodiment, whose primary difference to the embodiments of FIGS. 1A-C is the massage prong (24) is located outside of the pouch (16), rather than within the pouch, immersed in the medium (30). The prong (24) and pouch (34) are still both attached to the frame (18), such that the head (16) is removable from the handle (14). However, it is possible that the prong (24) may be permanently attached to the handle (14) in this embodiment. As can be seen, the prong (24) is still separated from direct contact with the skin (12), as the pouch (34) (shown in cross-section) still surrounds the prong (24) while separately containing the medium (30).

An alternate mechanism for connecting the massage head (16) to the handle (14) may include the use of one or more magnets. For example, the handle (14) may have one or more magnets configured to engage a ferrous material or other material attracted to magnets on or embedded in the frame (18), so that the frame (18) is drawn to and attached to the handle (14) when the magnet is brought into proximity with the ferrous material. Further, a steel ring imbedded into the frame (18) may be microwaved without dangerous sparks.

Figure 4A:
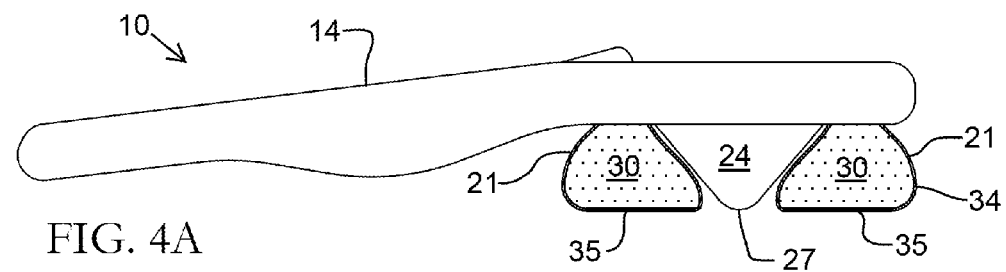
FIG. 4A-B is a side and bottom plan views of yet another embodiment of the massager, showing the massage head with the pouch in side cross-section.
Figure 4B:
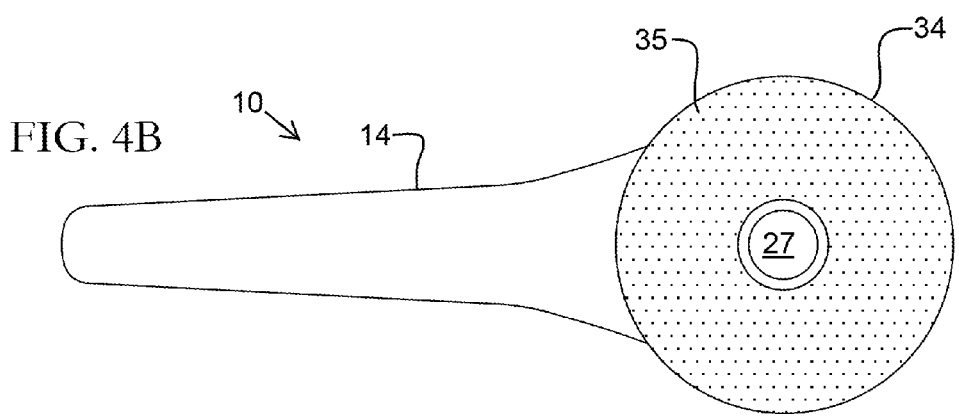

Looking at FIGS. 4A-B, again the prong (24) is outside of the pouch (34) and is not immersed in the medium (30). The pouch (34) in this embodiment may be donut-shaped, leaving a central hole (35) through which the prong (24) may make direct skin contact. The prong (24) is permitted to directly contact the skin, so both the pouch (34) and the prong together have direct skin contact. Thus, the pouch (34) heats or cools the area of the skin (12) immediately surrounding the prong (24).

Yet another alternate embodiment is shown in FIGS. 5A-B, where the handle (14) has within its forward tip (44) an offset rotating weight (40) on motor shaft (42). The forward tip (44) is inserted into a corresponding socket (42) formed within frame (18), as indicated by the arrow (43). In this way, the vibration created by the offset rotating weights (40) is more effectively transmitted to the massage head (16). Further, the offset rotating weight (40) vibration may be isolated from the handle by providing an isolating means on the shaft, such that the forward tip (44) is spaced apart and connected to the handle (14) through the isolating means. An example of a known isolating means is a coil spring.

Figure 6:
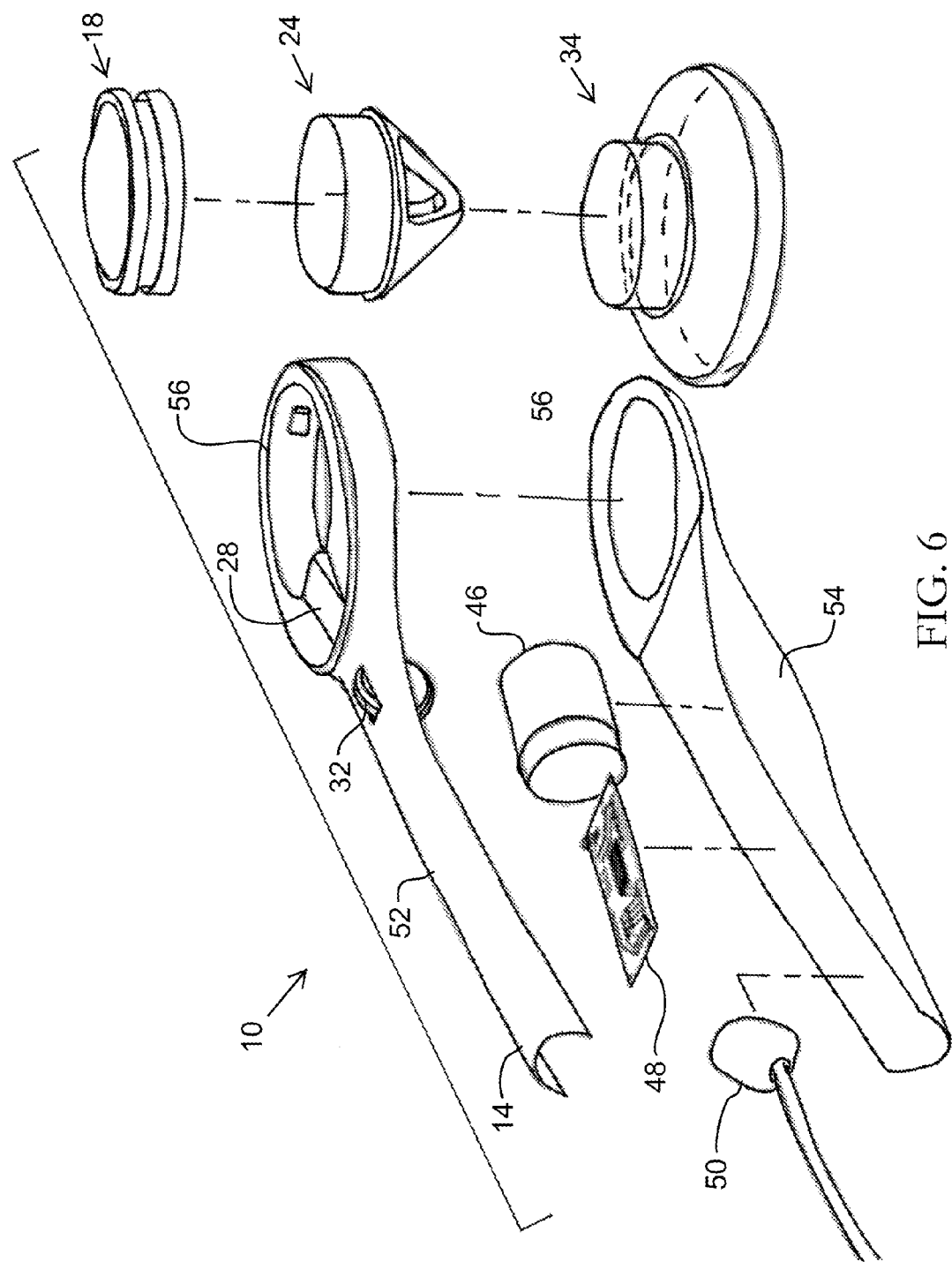
FIG. 6 is an exploded perspective view of an embodiment of the massager, showing the massage head and handle.

FIG. 6 shows a perspective exploded view of a an embodiment of the present massager (10) of FIGS. 1A-C and 2. The driver (46) can be a vibrating or percussive motor or actuator. A circuit board (48) is shown schematically, and is well known in the massager art, and may control the speed, frequency, and other massage parameters. An end cap (50) may serve as a strain gauge for holding an electrical cable to the handle (14). In this example, the massager (10) housing is made of a top half (52) connected to a bottom half (54). The pouch (34) may be formed into a mushroom-like shape by a blow molding or other suitable process. A compression ring (not shown) may be used to clamp about the neck of the pouch (34) to attach the pouch to the frame (18).

What is claimed is:

1. A massage device for massaging a surface area of a body, the massage device comprising:
    a massage prong having a tip for imparting a massage pressure on the surface area; and
    a pouch containing a liquid medium within a reservoir, the pouch having a bottom surface and a flexible sidewall connected to a frame, the massage prong being situated above the bottom surface with the bottom surface positioned between the tip and the surface area of the body when in use so that the massage pressure is imparted through the bottom surface;
    wherein the frame supports the pouch, the frame being detachable from a handle, the handle having a massage driver;
    wherein the pouch is positioned upon the surface area of the body with the bottom surface contacting the surface area;
    and wherein the bottom surface has an area substantially larger than the tip of the massage prong such that the tip can be moved laterally on the bottom surface, the side wall deforming with the movement of the tip so that the bottom surface remains substantially stationary relative to the surface area of the body.

2. The massage device of claim 1, wherein the massage prong is immersed within the liquid medium and permitted to move within the liquid medium.

3. The massage device of claim 1, wherein a second reservoir is formed between the reservoir and the bottom surface, the second reservoir containing a lubricant.

4. The massage device of claim 1, wherein the pouch may be brought in thermal contact with one of a heat source and a cold source, when the frame is detached from the handle.

5. The massage device of claim 1, wherein the massage driver is located within the handle at a terminus, the frame configured to receive the terminus, such that the massage driver is proximally located to the frame.

6. The massage device of claim 1, wherein a thermochromatic ink is distributed within the liquid medium, such that the color of the liquid medium changes in response to temperature.

7. The massage device of claim 1, wherein the liquid medium of the pouch is brought to a temperature different than the body temperature, the application of the pouch to the body affecting the body temperature.

8. The massage device of claim 1, wherein the frame has an prong opening for receiving the prong, the prong being attachable to the handle and being detachable from the frame.

9. The massage device of claim 8, wherein a top surface extends across the prong opening to form a prong cavity, when the frame is attached to the handle the prong extends though the prong opening and into the prong cavity, the tip of the prong acting through the top surface so that the massage pressure is imparted through the top surface and the bottom surface.

10. The massage device of claim 1, wherein the massage driver is one of a percussive driver and an offset weight driver.

11. A method for using a massage device, the method comprising the steps of:
    providing a massage device having a pouch with a liquid medium sealed within and a massage prong immersed within the pouch and capable of moving through the liquid medium relative to a wall of the pouch;
    changing the temperature of the liquid medium by bringing the pouch in thermal contact with a thermal source;
    applying the pouch to a surface area of a body; and
    imparting a massage force on the body by the massage prong operating though the wall and laterally moving relative to the wall; wherein the pouch is mounted to a frame and detachably connected to a handle having a massage driver.

12. The method for using a massage device of claim 11, wherein the thermal source is one of a microwave, a refrigeration unit, and a thermal plate.

13. The method for using a massage device of claim 11, further comprising the steps of:
    detaching the frame from the handle before bringing the pouch in thermal contact with a thermal source; and
    reattaching the frame to the handle before applying the pouch to the surface area of the body.

* * * * *